United States Patent [19]

Marsden et al.

[11] 4,002,651
[45] Jan. 11, 1977

[54] AZIDO-SILANE COMPOSITIONS

[75] Inventors: James Glenn Marsden, Amawalk; Peter Joseph Orenski, Ossining, both of N.Y.

[73] Assignee: Union Carbide Corporation, New York, N.Y.

[22] Filed: June 26, 1974

[21] Appl. No.: 483,367

[52] U.S. Cl. .............................. 260/349; 428/446; 428/447; 428/450
[51] Int. Cl.$^2$ .......................................... C07C 11/7
[58] Field of Search .................. 260/349; 428/251

[56] References Cited
UNITED STATES PATENTS

| | | | |
|---|---|---|---|
| 3,697,551 | 8/1972 | Thomson | 260/349 |
| 3,706,592 | 12/1972 | Thomson | 428/251 |

*Primary Examiner*—Lewis Gotts
*Assistant Examiner*—Cary Owens
*Attorney, Agent, or Firm*—Reynold J. Finnegan

[57] ABSTRACT

Azido-containing silane compositions of matter useful as coupling agents in the production of polymer composite articles.

11 Claims, No Drawings

AZIDO-SILANE COMPOSITIONS

BACKGROUND OF THE INVENTION

This invention relates to novel azido-silane compositions of matter and their uses.

While the prior art has heretofore disclosed azido-containing silane compounds, e.g., U.S. Pat. Nos. 3,705,911 and 3,706,592, it has not been found to disclose or utilize the action of the azido-silane compositions of matter of this invention.

SUMMARY OF THE INVENTION

It has now been discovered that novel-azido-silane compositions of matter can be prepared which have the advantage of being easily soluble, particularly in water, thus rendering them especially suitable as coupling agents for the glass finishing industry.

Accordingly, it is an object of this invention to provide novel azido-silane compositions of matter. It is another object of this invention to provide composite articles comprising a filler or reinforcement base member and a polymeric matrix. Other objects and advantages of this invention will become readily apparent from the following description and appended claims.

More specifically, one aspect of this invention is directed to a solubilized azido-containing silane composition of matter produced by a process which comprises reacting in the presence of a solvent (a) an azido-containing compound selected from the group consisting of carboxylic acids of the formula

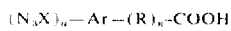

and the ammonium salts of said acids, wherein X is a radical selected from the group consisting of sulfonyl and formyl radicals, $a$ is an integer of from 1 to 2, Ar is an aryl or hydroxy-substituted aryl radical, R is an alkylene radical and $n$ has a value of 0 or 1; and (b) an amino-containing silane having the formula

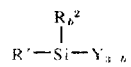

wherein $R^2$ is a monovalent hydrocarbon radical, $b$ has a value of from 0 to 2, Y is a hydrolyzable group selected from the class consisting of alkoxy and aryloxy radicals, and R' is an organic radical directly bonded to the silicon atom of said silane through a carbon to silicon bond, said organic radical further containing at least one nitrogen atom, said solvent being present in an amount sufficient to solubilize the azido-containing silane product of (a) and (b).

DESCRIPTION OF THE PREFERRED EMBODIMENTS

The azido-containing compounds, and/or methods for their production, employed in the instant invention are well known in the art. As pointed out such compounds include carboxylic acids of the formula

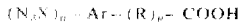

and the ammonium salts of said acids, wherein X is a radical selected from the group consisting of sulfonyl ($SO_2$) and formyl (COO) radicals, $a$ is an integer of from 1 to 2, Ar is an aryl radical or a hydroxy-substituted aryl radical, preferably phenylene or hydroxyphenylene, R is an alkylene radical having from 1 to 17 carbon atoms, and $n$ has a value of 0 to 1, preferably 0. The most preferred acids are those containing the azidosulfonyl radical. Among the more preferred azido-containing compounds are

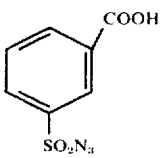

3-(azidosulfonyl) benzoic acid,

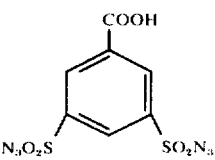

3,5-di(azidosulfonyl) benzoic acid,

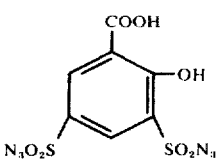

3,5-di(azidosulfonyl) salicylic acid,

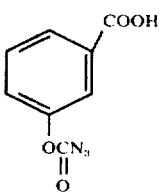

3-(azidoformyl) benzoic acid,

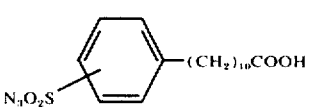

(azidosulfonyl)-omega-phenyleneundeconoic acid,

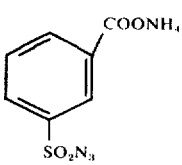

ammonium salt of 3-(azidosulfonyl)benzoic acid, and the like.

The disulfonyl azido containing carboxylic acids such as 3,5-di(azidosulfonyl) benzoic acid and 3,5-di(azidosulfonyl) salicylic acid are considered to be novel compounds per se as witnessed by concurrently filed U.S. Application, Ser. No. 483,376 filed June 26, 1974, and now U.S. Pat. No. 3940427.

The amino-containing silane compounds, and/or methods for their preparation, employed in the instant invention are also well known in the art. As pointed out above, such silanes include those of the formula

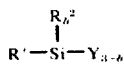

wherein $R^2$ is a monovalent hydrocarbon radical having from 1 to 12 carbon atoms, $b$ has a value of 0 to 2, preferably 0, Y is a member selected from the class consisting of alkoxy and aryloxy radicals having from 1 to 12 carbon atoms and wherein R' is an organic radical directly bonded to the silicon atom of said silane through a carbon to silicon bond, said organic radical further containing at least one nitrogen atom.

Illustrative of R' are any organic radicals directly bonded to the silicon atom of said silane through a carbon to silicon bond, said organic radical further containing at least one nitrogen atom. For instance among the more preferred organic radicals are those selected from the group consisting of aminoalkylene radicals such as aminomethyl, beta-aminoethyl, gamma-aminopropyl, gamma-N,N-dimethyl aminopropyl, delta-aminobutyl, and the like; amino aryl radicals such as aminophenyl, and the like; alkylene polyamine radicals such as N-(beta-aminoethyl)-gamma-aminopropyl, N-(beta-aminoethyl-aminoethyl), N-(gamma-aminopropyl)-gamma-aminoisobutyl, N-beta-amino (polyethyleneimine) propyl, and the like; and polyazamide radicals such as taught in U.S. Pat. No. 3,746,738

Most preferably R' represents an amino radical of the formula

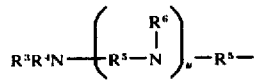

wherein $R^3$, $R^4$ and $R^6$ individually represent a radical selected from the group consisting of hydrogen and a monovalent hydrocarbon radical having from 1 to 12 carbon atoms, at least one $R^3$, $R^4$ and $R^6$ group being hydrogen, and each $R^5$ group individually represents a divalent alkylene radical having from 1 to 10 carbon atoms, such as methylene, ethylene, propylene, butylene, hexylene, decylene, and the like, and $y$ is 0 or a positive integer, preferably $y$ has a value of 0 to 4. Preferably $R^5$ is a divalent alkylene radical having from 2 to 6 carbon atoms especially ethylene and propylene.

Illustrative monovalent hydrocarbon radicals that may be represented by $R^2$, $R^3$, $R^4$ and $R^6$ include such radicals as alkyl (e.g., methyl, ethyl, propyl, pentyl, dodecyl, and the like); cycloalkyl as cyclobutyl, cyclohexyl, and the like; aryl (such as phenyl, naphthyl, biphenyl, and the like); alkaryl (such as 4-methylphenyl, 2,4-diethylphenyl, and the like); arylalkyl (such as benzyl, beta-phenylethyl, and the like); and the like. Preferably, the monovalent hydrocarbon radical is a member selected from the group consisting of phenyl and lower alkyl radicals of 1 to 4 carbon atoms, especially a methyl radical.

Illustrative of Y groups are alkoxy radicals (such as methoxy, ethoxy, propoxy, isopropoxy, dodecyloxy, and the like), and aryloxy radicals (such as phenoxy, naphthyloxy, biphenyloxy, and the like). Preferably Y is a lower alkoxy radical of 1 to 4 carbon atoms, especially methoxy or ethoxy.

Silane compounds that can be employed in accordance with this invention include those descibed in U.S. Pat. Nos. 2,832,754; 2,942,019, 2,971,864; 3,321,350; and 3,746,738, the disclosures of which are incorporated herein by reference thereto. Specific examples of such amino-containing silane compounds include
aminomethyltrimethoxysilane
gamma-aminopropyltrimethoxysilane,
gamma-methylaminopropyltrimethoxysilane,
gamma-ethylaminopropyltrimethoxysilane,
gamma-N,N-dimethylaminopropyltrimethoxysilane,
gamma-aminopropyltriethoxysilane,
gamma-aminopropyltripropoxysilane,
gamma-aminopropylmethyldiethoxysilane,
gamma-aminopropylethyldiethoxysilane,
gamma-aminopropylphenyldiethoxysilane,
gamma-aminoisobutyltrimethoxysilane,
delta-aminobutyltriethoxysilane,
delta-aminobutylmethyldiethoxysilane,
beta-aminoethyltriethoxysilane,
epsilon-aminopentylphenyldibutoxysilane,
N-(beta-aminoethyl)-gamma-aminopropyltrimethoxysilane,
N-(beta-dimethylaminoethyl)-gamma-aminopropyltrimethoxysilane,
N-(beta-aminoethylaminoethyl)-gamma-aminopropyltrimethoxysilane,
N-(gamma-aminopropyl)-gamma-aminoisobutylmethyldiethoxysilane,
N-(beta-aminoethyl)-gamma-aminopropyltriethoxysilane,
1,4-aminophenyltrimethoxysilane,
beta-amino(polyethyleneimine) propyltrimethoxysilane, silane containing polyazamides obtained e.g. by reacting a gamma-glycidoxypropyl-trimethoxysilane with a polyazamide polymer as taught in U.S. Pat. No. 3,746,738, and the like. The most preferred silanes are those wherein $R^3$, $R^4$ and $R^6$ are hydrogen atoms, especially gamma-aminopropyltriethoxysilane and N-beta—(aminoethyl)-gamma-aminopropyltrimethoxysilane.

The solvent employed by the instant invention can be any oxygen-containing solvent that will solubilize the product mixture of the azido-containing carboxylic acid and silane compounds used herein. Such solvents include water, and conventional organic solvents such as hydroxy-containing compounds (e.g. alcohols such as ethanol, propanol and the like); ethers (such as diethylether, dipropylether, and the like); ketones (such as acetone, methylethylketone, diethylketone, and the like); and the like. Preferably the solvent is water or ethanol, water being the most preferred solvent. The amount of solvent employed is not narrowly critical and obviously need only be at least that amount sufficient to solubilize the azido-containing silane composition of matter product and of course merely depends on the starting materials employed. Of course higher amounts of solvent can be employed if desired.

The azido-silane compositions of this invention are most conveniently prepared as solvent solutions by first intoducing into the solvent the amino-containing silane compound and then adding with stirring the azido-containing compound to form the solubilized product mixture of said compounds as witnessed by the clear product solution obtained. The azido-containing compound and amino-containing silane compound are employed in substantially equal molar quantities, that is to say from about 0.9 to about 1.1 moles of azido-containing compound to about 1.1 to about 0.9 moles of amino-containing silane. While it is generally preferred to employ azido-containing carboxylic acids, alternatively if desired the azido-silane compositions of matter of this invention can also be prepared by employing an ammonium salt of the azido-containing carboxylic acid. For instance ammonia, either as a gas or a water concentrate, can first be introduced into the solvent followed by the addition of the azido-containing carboxylic acid to form the solubilized ammonium salt of said acid, followed by the addition of the amino-containing silane to the solution with stirring to form the solubilized product mixture of the two compounds as witnessed by the clear product solution obtained. The conditions of the mixing procedure to produce the azido-silane compositions of this invention are not critical. For instance the order of addition of ingredients may be varied and the mixing may be conducted at any suitable temperature and pressure. Normally the mixing procedure is merely carried out at room temperature (20° C–30° C.) and atmospheric pressure. If desired an azido-silane product solution may be first formed in one solvent (e.g. ethanol) and then the dried salt obtained therefrom added to a different solvent (e.g. water). Of course it is obvious that mixtures of different solvents, different azido-containing compounds and/or different amino-containing silanes can be employed if desired.

Of course it is understood that since the amino-containing silane compounds employed in this invention contain hydrolyzable groups (e.g. alkoxy radicals) the solubilized azido-silane product mixture compositions of this invention include and encompass the hydrolyzates and condensates of said azido-silane product. Thus while the precise structural configuration of the product mixture of the solubilized azido-silane compositions of this invention is not determinable, it is apparent that the product mixture represents novel ionic azido-silane compounds. However, for want of an illustration it is considered that, if desired, generic type ionic structures may be given to the product mixtures of the solubilized azido-silane compositions of this invention. For example the product mixture of 3-(azidosulfonyl) benzoic acid and gamma-aminopropyltriethoxysilane might be represented by the formula

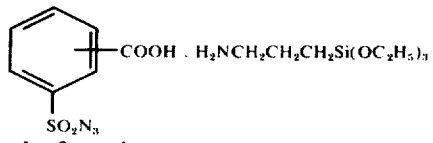

or by the formula

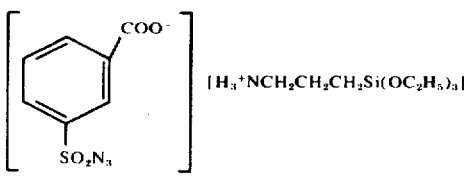

Of course it is to be understood that in addition to the above mentioned solubilized azido-containing silane composition, the instant invention also includes the azido-containing compounds obtained upon removal of the solvent. Clearly the solvent can be removed if desired, e.g. for the purpose of shipping or storage of a solid product, and the procedure employed for removal of the solvent is obviously not critical, any conventional method desired can be used, such as evaporation of the solvent, and the like.

The azido-silane compositions of matter of this invention can be used as coupling agents to enhance the adhesion of various substrates with a broad variety of polymers. The use of coupling agents to promote such bonding is well known in the art as witnessed for example by U.S. Pat. Nos. 2,832,754; 2,971,864; 3,258,477; 3,661,628; 3,671,562; 3,705,911; 3,706,592, and the like, the disclosures of which are incorporated herein the reference thereto.

More particularly the azido-silane compositions of matter of this invention have been found to useful in promoting coupling and bonding between inorganic substrates, such as siliceous, metallic or metallic oxide materials and organic polymers.

Materials or substrates to which the organic polymers may be bonded include, siliceous materials such as glass, asbestos, sand, clay, talc, Wollastonite (calcium meta-silicate), feldspar, concrete, ceramic materials, and the like; metals such as aluminum, copper, cadmium, chromium, magnesium, nickel, silver, tin, titanium, zinc, and the like; the alloys of such metals as brass, bronze, steel, and the like including metals which have been surface treated with phosphates, chromates, and the like; metal oxides such as aluminum oxide, iron oxides, lead oxides, titanium dioxide, zinc oxide and the like. If desired the organic polymers can even be bonded to other polymers through the azido-silane coupling agents. Of course it is understood that the particular configuration of the inorganic substrate to which the organic polymer is bonded is not critical and that the inorganic materials can be in any various form such as sheets, plates, blocks, wires, cloth, fibers, filaments, particles, powders, and the like.

Organic polymers that may be bonded to such inorganic substrates are well known in the art and include any of a wide variety of polymers mentioned in the patents cited above. Illustrative of some of the more preferred polymers are thermoplastic resins such as polyethylene, polypropylene, polystyrene, poly-(vinyl chloride), polycarbonates, polyesters, nylon, polyacrylonitrile, and the like, as well as copolymers and terpolymers thereof; thermoset resins such as unsaturated polyesters, epoxies, phenolics, melamine, and the like; elastomers such as natural rubber, styrene butadiene rubber, neoprene, ethylene propylene monomer rubber, ethylene propylene diene (e.g., hexadiene, ethylidene norborene, etc.) rubber, and the like. The particular form of the organic polymer is not critical. The most preferred organic polymers are polyolefin thermoplastic resins especially, polypropylene.

The procedures and conditions employed in bonding organic polymers and substrates through the use of coupling agents are well known in the art and any conventional method can be employed with the azido-silane compositions of this invention.

Thus as pointed out above an additional object of this invention can be described as an article of manufacture comprising a substrate selected from the group consisting of siliceous materials, metals, metal oxides and polymers coated with the novel azido-silane compositions of matter of this invention. Further articles of manufacture comprise an organic polymer bonded to a substrate selected from the group consisting of siliceous materials, metals, metal oxides and polymers through an azido-silane composition of matter of this invention. As pointed out above the most preferred substrate is a siliceous material, preferably glass and fiberglass, while the preferred organic polymer is a polyolefin, especially polypropylene.

As pointed out the process employed in preparing the articles of manufacture of this invention is not critical and any conventional process can be employed. For example the material or substrate can be coated with an azido-silane composition of matter of this invention, allowed to dry and then coated with the organic polymer followed by curing the polymer on the coated substrate. Alternatively the azido-silane and the organic polymer can be deposited together on the substrate and then cured or the polymer can be first treated with the azido-silane compound and then coated onto the substrate and cured.

Thus there is provided a coupling agent at the interface of the substrate and organic polymer, said coupling agent being the azido-silane reaction products, their hydrolyzates and condensates of this invention. The temperature at which the bonding reaction is carried out can be varied over a wide range depending upon the specific compounds employed. In general heat temperatures will normally be in the range of from about 100° C. to about 350° C. or higher. If desired, the bonding between the substrate, azido-silane compositions and organic polymer may also be carried out by the use of ultra-violet light radiation, X-rays, and the like. The various amounts of compounds employed of course merely depend upon the azido-silane employed, the surface area to be covered, the organic polymer to be bonded to the material, and the like. The method of coating the substrate is not critical and the azido-silane compositions of this invention can be sprayed, brushed, poured or rolled on to the surface of the material, and the like, or alternatively the material or substrate can be dipped into the solution of the azido-silane compositions of this invention. Thus it will be readily apparent to those skilled in the art that the azido-silane compositions of matter of this invention lend themselves to any conventional process where organic polymers are to be bonded to substrates such as siliceous materials, metals, metal oxides and other polymers.

The azido-silane compositions of matter of this invention have a number of advantages. For example, the azido-silanes are easily soluble in water and this feature renders them especially suitable for use as size binders in the glass finishing industry where water is overwhelmingly the preferred solvent. The azido-silane compositions are also very stable even under acidic conditions. Moreover the physical properties and characteristics, such as flexural strength, falling dart impact, heat distortion temperature, and the like, of the resulting composites have been found to be considerably bettered as a result of the improved bonding between the organic polymer and substrate brought about by the action of the azido-silane compositions of this invention.

By way of theory, which applicants do not wish to be bound, it is believed that the functional groups on the silicon portion of the azido-silane provide the enhanced adhesion to the substrate while the azido moiety is believed to couple with the CH bonds of the organic polymer to achieve the most intimate bond possible between the polymer and the substrate. For instance, when a two-step procedure is employed for supplying an azido-silane composition and an polyolefinic polymer on the substrate surface, azido-silane compositions of matter of this invention may be illustrated by the following exemplative equations

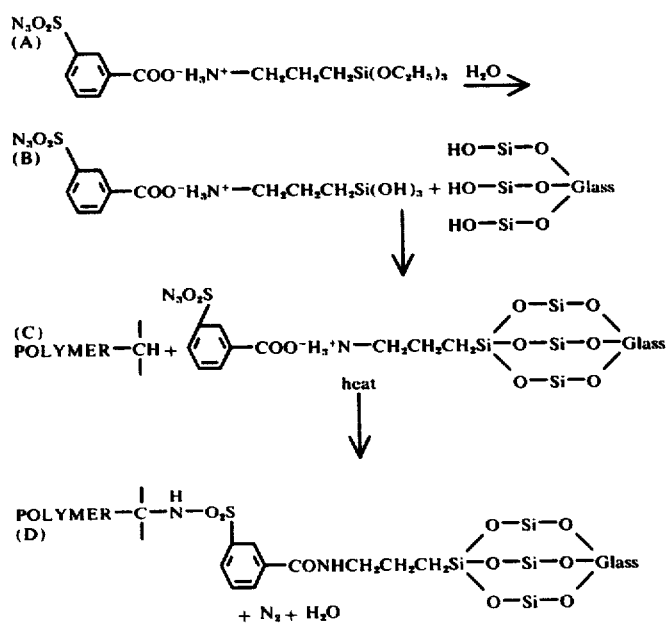

The following examples are illustrative of the present invention and are not to be regarded as limitative. It is to be understood that all of the parts, percentages and proportions referred to herein and in the appended claims are by weight unless otherwise indicated.

EXAMPLE A 8.0 grams (123 milimoles) of sodium azide dissolved in 25 ml. of water were added to 16 grams (50 milimoles) of 3,5-di(chlorosulfonyl)benzoic acid, m.p. 181°–183° C., dissolved in 80 ml. of acetone. The addition was conducted at 2°–5° C. over 10 minutes and then the reaction mixture stirred for one-half hour at 2°–5° C. before being added to 500 ml. of ice water. The cloudy solution was extracted with two 250 ml. portions of ethyl ether, then the ether extracts were combinded and dried over anhydrous magnesium sulfate and the ether stripped under vacuum. There was obtained 9.0 grams (a 54 per cent yield) of desired 3,5-di(azidosulfonyl)benzoic acid product which was a yellowish solid having a melting point of 118°–121° C. Infrared and nuclear magnetic resonance analysis verified the product to be 3,5-di(azidosulfonyl) benzoic acid.

EXAMPLE B 14.3 grams (0.22 mole) of sodium azide dissolved in 40 ml. of water were added to 33.5 grams (0.1 mole) of 3,5-di(chlorosulfonyl) salicylic acid, m.p. 184°–186° C., dissolved in 150 ml. of acetone. The addition was conducted at 0° to 5° C. over five minutes and then the reaction mixture stirred for one-half hour at 0° to 5° C. The solution was filtered and the upper (acetone) layer of the filtrate separated and dried over anhydrous magnesium sulfate. The acetone was then stripped under vacuum and replaced with 200 ml. of benzene to give a cloudy solution containing some solids. The solution was filtered, the volume of filtrate reduced 80 ml. by evaporation and allowed to crystallize. The crystals were isolated by filtration and dried under vaccuum at 65° C. There was obtained an eight-five per cent yield (29.5 grams) of desired 3,5-di(azidosulfonyl)salicylic acid product which decomposed in a capillary tube starting at 165° C. without melting and became a dark brown mass at 210° C. Infrared and nuclear magnetic resonance analysis verified the product to be 3,5-di(azidosulfonyl)salicylic acid.

EXAMPLE C 130 ml. of chlorosulfonic acid were added with stirring to 26.2 grams (0.1 mole) of omega-phenylundecanoic acid dissolved in 130 ml. of chloroform, which had been cooled to 0° C., over 25 minutes. After the evolution of HCl subsided, the mixture was brought to room temperature, stirred for 45 minutes and poured into 1000 ml. of ice-water. The milky chloroform layer was separated and dried over anyhydrous magnesium sulfate and the solvent stripped to yield a milky, viscous liquid.

The viscous liquid obtained was dissolved in 150 ml. of acetone, cooled to 0° C. and then 7.1 grams (0.11 mole) of sodium azide in 40 ml. of water were added. The mixture was stirred at 0° C. for one-half hour after which the acetone layer was separated, dried over anhydrous magnesium sulfate and solvent stripped. There was obtained an 80% yield of desired (azidosulfonyl)-omega-phynylundecanoic acid product. The product was an opaque semi-solid was found to have a carboxyl content of 12.00 per cent (theory = 12.26%). Infrared and nuclear magnetic resonance analysis verified the product to be (azidosulfonyl)-omega-phenylundecanoic acid.

EXAMPLE 1

Three milimoles (0.66 grams) of gamma-aminopropyltriethoxysilane were dissolved at room temperature in 99 grams of distilled water. The solution was clear and had a pH of 10.5 Then three milimoles (0.68 grams) of 3-(azidosulfonyl)benzoic acid were added at room temperature with vigorous stirring. The solution was cloudy at first because the benzoic acid is water insoluble, but the solution cleared within 5 minutes as the ionic azido-silane product solution formed. The product solution had a pH of 8.2 and remained clear and stable for at least a week.

EXAMPLE 2

Acetic acid was added at room temperature to the azido-silane product solution of Example 1 until the pH had decreased to 4.5. The acidified solution remained clear and stable for at least a week.

EXAMPLE 3

Example 1 was repeated using 97 grams of water, 9 milimoles (1.98 grams) of gamma-aminopropyltriethoxysilane and 9 milimoles (2.04 grams) of 3-(azidosulfonyl) benzoic acid. A clear azido-silane product solution was formed having a final pH of 7.8. Acetic acid was added at room temperature to the product solution until the pH had decreased to 4.5 and the solution remained clear.

EXAMPLE 4

Example 1 was repeated using 95 grams of water, 15 milimoles (3.30 grams) of gamma-aminopropyltriethoxysilane and 15 milimoles (3.40 grams) of 3-(azidosulfonyl)benzoic acid. A clear azido-silane product solution was formed having a final pH of 7.9.

EXAMPLE 5

Example 1 was repeated using 95 grams of water, 13.1 milimoles (2.90 grams) of N-(beta-aminoethyl)-gamma-aminopropyltrimethoxysilane and 13.2 milimoles (3.00 grams) of 3-(azidosulfonyl)benzoic acid. A clear azido-silane product solution was formed having a final pH of 8.0.

EXAMPLE 6

Example 1 was repeated using 490 grams of water, 4.3 grams of a polyazamide polymer derived from ethylene diamine and containing originally 7.9 moles/kg. of primary and secondary amine of which 2.1 moles/kg. had been modified with gamma-glycidoxypropyltrimethoxysilane as taught in U.S. Pat. No. 3,746,738 and 5.7 grams of 3-(azidosulfonyl)benzoic acid. A clear pale yellow azido-silane product solution was obtained.

EXAMPLE 7

Example 1 was repeated using 142.5 mg. of 200 proof ethanol instead of water, 64 mg. of gammaaminopropyltriethoxysilane and 60 mg. of 3-(azidosulfonyl)-benzoic acid. One drop of the clear azidosilane product solution formed was then placed on a potassium bromide infrared plate and the ethanol solvent removed in a stream of dry nitrogen. The infrared spectrum substantiated the formation of the ionic salt of said silane and benzoic acid by showing the complete disappearance of the carboxy carbonyl band at 1695–1700 cm$^{-1}$ that is present in the azidocontaining benzoic acid starting material and the appearance of the characteristic salt bands, that is a broad band (—NH₃+) between 3300 and 2200 cm⁻¹ and the ionized carbonyl band at 1595–1600 cm⁻¹.

EXAMPLE 8

200 mg. of a 29 percent by weight ammonium hydroxide aqueous solution (3.4 milimoles NH$_3$) were added at room temperature to 98 grams of distilled water followed by 0.68 grams (3 milimoles) of 3-(azidosulfonyl)benzoic acid with stirring. The solution was at first cloudy, but cleared quickly as the water-soluble 3-(azidosulfonyl)benzoic acid ammonium salt,

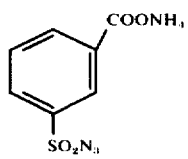

formed. 0.66 grams (3 milimoles) of gamma-aminopropyltriethoxysilane were then added at room temperature to the clear solution with stirring for five minutes to form a clear azido-silane product solution of said ammonium salt and said silane which can be used to treat glass cloth.

EXAMPLE 9

A clear, stable azido-silane product solution was prepared by repeating Example 8, except that 98 grams of ethanol were used as the solvent instead of water.

EXAMPLE 10

A 2 wt. % aqueous azido-silane product solution of gamma-aminopropyltriethoxysilane and 3-(azidosulfonyl) benzoic acid prepared as in to Example 1 was used to finish 4 thirteen inch wide swatches of heat-cleaned glass fabric. At 50 wt. % wet pickup, 1 wt. % solids based on fabric weight was deposited on the glass surface. All swatches were then air dried for four hours and used to prepare a dry sandwich laminate by alternating eleven plies of finished glass fabric and twelve plies of 0.010 inch polyethylene film. The laminate was then pressed to stops in a pre-heated press for 30 minutes at 400° F. The pressed laminate was cut in ½ × 4 in. test specimens with the 4 inch dimension parallel to the fabric warp direction and tested for flexural strength, both initally and after immersion in water, according to ASTM Specification D-790 using a Baldwin-Tate Tester.

The test specimens showed an initial flexural strength of 20,900 psi. and a flexural strength of 19,400 psi. after 16 hours in 122° F. water. By comparison a polyethylene-glass laminate prepared from unfinished heat-cleaned glass fabric had an initial flexural strength of 10,200 psi. and a flexural strength of 6,400 psi. after 16 hours in 122° F. water; a polyethylene-glass laminate prepared from gamma-aminopropyltriethoxysilane finished glass fabric had an initial flexural strength of 22,600 psi. and a flexural strength of 17,600 psi. after 16 hours in 122° F. water; a polyethylene-glass laminate prepared from 3-(azidosulfonyl) benzoic acid finished glass fabric had an initial flexural strength of 17,400 psi. and a flexural strength of 8,900 psi. after 16 hours in 122° F water; and a polyethylene-glass laminate prepared from gamma-methacryloxypropyltrimethoxysilane finished glass fabric had an initial flexural strength of 19,500 psi and a flexural strength of 18,900 psi after 16 hours in 122° F. water.

EXAMPLE 11

A 2 wt.% aqueous azido-silane product solution of gamma-aminopropyltriethoxysilane and 3-(azidosulfonyl) benzoic acid prepared as in Example 1 was used to finish 4 thirteen inch wide swatches of heat-cleaned glass fabric. At 50 wt.% wet pickup, 1 wt.% solids based on fabric weight was deposited on the glass surface. All the swatches were then air dried for four hours and used to prepare a dry sandwich laminate by alternating eleven plies of finished glass fabric and twelve plies of 0.010 inch polypropylene film. The laminate was then pressed to stops in a pre-heated press for 30 minutes at 475° F. The pressed laminate was cut in ½ × 4 inch test specimens with the 4 inch dimension parallel to the fabric warp direction and tested for flexural strength, both initially and after immersion in water, according to ASTM Specification D-790 using a Baldwin-Tate Tester.

The test specimens showed an initial flexural strength of 30,700 psi. and a flexural strength of 25,100 psi. after 16 hours in 122° F. water. By comparison a polypropylene-glass laminate prepared from unfinished heat-cleaned glass fabric had an initial flexural strength of 12,700 psi. and a flexural strength of 9,600 psi. after 16 hours in 122° F. water; a polypropylene-glass laminate prepared from gamma-aminopropyltriethoxysilane finished glass fabric had an initial flexural strength of 21,800 psi. and a flexural strength of 14,300 psi. after 16 hours in 122° F. water; a polypropylene-glass laminate prepared from 3-(azidosulfonyl) benzoic acid finished glass fabric had an initial flexural strength of 23,700 psi. and a flexural strength of 11,100 psi. after 16 hours in 122° F. water and a polypropylene-glass laminate prepared from gamma-methacryloxypropyltrimethoxysilane finished glass fabric had an initial flexural strength of 17,900 psi. and a flexural strength of 16,900 psi. after 16 hours in 122° F.

EXAMPLE 12

A 2 wt.% aqueous azido-silane product solution of gamma-aminopropyltriethoxysilane and 3-(azidosulfonyl) benzoic acid prepared as in Example 1 was used to finish 4 thirteen inch wide swatches of heat-cleaned glass fabric. At 50 wt.% wet pickup, 1 wt.% solids based on fabric weight was deposited on the glass surface. All the swatches were then air dried for four hours and used to prepare a dry sandwich laminate by alternating eleven plies of finished glass fabric and twelve plies of 0.01 inch polyacetal film. The laminate was then pressed to stops in a pre-heated press for 30 minutes at 420° F. The pressed laminate was cut in ½ × 4 inch test specimens with the 4 inch dimension parallel to the fabric warp direction and tested for flexural strength, both initially and after immersion in water, according to ASTM Specification D-790 using a Baldwin-Tate Tester.

The test specimens showed an initial flexural strength of 35,500 psi. and a flexural strength of 31,200 psi. after 16 hours in 122° F water. By comparison a polyacetal-glass laminate prepared from unfinished heat-cleaned glass fabric had an initial flexural strength of 25,800 psi. and a flexural strength of 14,500 psi. after 16 hours in 122° F. water, a polyacetal-glass laminate prepared from gamma-aminopropyltriethoxysilane finished glass fabric had an initial flexural strength of 23,200 psi and a flexural strength of 19,800 psi. after 16 hours in 122° F. water; and a polyacetal-glass laminate prepared from gamma-N,N-bis(2-hydroxyethyl)-aminopropyltriethoxysilane finished glass fabric had an initial strength of 26,100 psi. and a flexural strength of 21,100 psi. after 16 hours in 122° F water.

EXAMPLE 13

A 2 wt.% aqueous azido-silane product solution of gamma-aminopropyltriethoxysilane and 3-(azidosulfonyl) benzoic acid prepared as in Example 1 was used to finish 4 thirteen inch wide swatches of heat-cleaned glass fabric. At 50 wt.% wet pickup, 1 wt.% solids based on fabric weight was deposited on the glass surface. All the swatches were then air dried for four hours and used to prepare a dry sandwich laminate by alternating eleven plies of finished glass fabric and twelve plies of 0.010 inch polycarbonate film. The laminate was then pressed to stops in a pre-heated press for 30 minutes at 450° F. The pressed laminate was cut in ½ × 4 inch test specimens with the 4 inch dimension parallel to the fabric warp direction and tested for flexural strength, both initially and after immersion in water, according to ASTM Specification D-790 using a Baldwin-Tate Tester.

The test specimens showed an initial flexural strength of 41,700 psi. and a flexural strength of 40,600 psi. after 16 hours in 122° F. water. By comparison a polycarbonate-glass laminate prepared from unfinished heat-cleaned glass fabric had an initial flexural strength of 34,400 psi. and a flexural strength of 26,700 psi. after 16 hours in 122° F. water; a polycarbonate-glass laminate prepared from gamma-aminopropyltriethoxysilane finished glass fabric had an initial flexural strength of 35,700 psi and a flexural strength of 31,200 psi. after 16 hours in 122° F water; and a polycarbonate-glass laminate prepared from 3-(azidosulfonyl) benzoic acid finished glass fabric had an initial flexural strength of 39,600 psi. and a flexural strength of 17,100 psi. after 16 hours in 122° F. water.

EXAMPLE 14

A 2 wt.% aqueous azido-silane product solution of gamma-aminopropyltriethoxysilane and 3-(azidosulfonyl) benzoic acid prepared as in Example 1 was used to finish 4 thirteen inch wide swatches of heat-cleaned glass fabric. At 50 wt. % wet pickup, 1 wt. % solids based on fabric weight was deposited on the glass surface. All the swatches were then air dried for four hours and used to prepare a dry sandwich laminate by alternating eleven plies of finished glass fabric and twelve plies of 0.010 inch polystyrene film. The laminate was then pressed to stops in a preheated press for 30 minutes at 475° F. The pressed laminate was cut in ½ × 4 inch test specimens with the 4 inch dimension parallel to the fabric warp direction and tested for flexural strength, both initally and after immersion in water, according to ASTM Specification D-790 using a Baldwin-Tate Tester.

The test specimens showed an initial flexural strength of 52,200 psi. and a flexural strength of 40,900 psi. after 16 hours in 122° F. water. By comparison a polystyrene-glass laminate prepared from unfinished heat-cleaned glass fabric had an initial flexural strength of 24,800 psi. and a flexural strength of 19,300 psi. after 16 hours in 122° F. water; a polystyrene-glass laminate prepared from gamma-aminopropyltriethoxysilane finished glass fabric had an initial flexural strength of 37,700 psi. and a flexural strength of 29,200 psi. after 16 hours in 122° F. water; and a polystyrene-glass laminate prepared from 3-(azidosulfonyl) benzoic acid finished glass fabric had an initial flexural strength 47,800 psi. and a flexural strength of 19,000 psi. after 16 hours in 122° F. water.

EXAMPLE 15

A 2 wt. % aqueous azido-silane product solution of gamma-aminopropyltriethoxysilane and 3-(azidosulfonyl) benzoic acid prepared as in Example 1 was used to finish 4 thirteen inch wide swatches of heat-cleaned glass fabric. At 50 wt. % wet pickup, 1 wt. % solids based on fabric weight was deposited on the glass surface. All the swatches were then air dried for four hours and used to prepared a dry sandwich laminate by alternating eleven plies of finished glass fabric and twelve plies of 0.010 inch poly(vinylchloride) film. The laminate was then pressed to stops in a pre-heated press for 20 minutes at 350° F. The pressed laminate was cut in ½ × 4 inch test specimens with the 4 inch dimension parallel to the fabric warp direction and tested for flexural strength, both initially and after immersion in water, according to ASTM Specification D-790 using a Baldwin-Tate Tester.

The test specimens showed an initial flexural strength of 17,600 psi. and a flexural strength of 14,800 psi. after 16 hours in 122° F. water. By comparison a poly(-vinyl chloride) glass laminate prepared from unfinished heat-cleaned glass fabric had an initial flexural strength of 8,600 psi. and a flexural strength of 8,800 psi. after 16 hours in 122° F. water, a poly(vinyl chloride)-glass laminate prepared from gamma-aminopropyltriethoxysilane finished glass fabric had an initial flexural strength of 14,800 psi. and a flexural strength of 13,700 psi. after 16 hours in 122° F. water and a poly(vinyl chloride)-glass laminate prepared from 3-(axidosulfonyl) benzoic acid finished glass fabric had an initial flexural strength of 12,500 psi. and a flexural strength of 9,800 psi. after 16 hours in 122° F. water.

EXAMPLE 16

A clear, stable 2 wt. % acetone azido-silane product solution was formed by dissolving 3.1 grams of gamma-aminopropyltriethoxysilane in 147 grams of acetone at room temperature and then adding 4.9 grams of 3,5-di(azidosulfonyl) salicylic acid with vigorous stirring.

EXAMPLE 17

The azido-silane product solution of Example 16 was used to prepare a glass-polypropylene laminate by following the procedure of Example 11.

The test specimens showed a flexural strength of 24,700 psi. By comparison a polypropylene-glass laminate prepared from unfinished heat-cleaned glass fabric had a flexural strength of 12,700 psi; a polypropylene-glass laminate prepared from gamma-aminopropyltriethoxysilane finished glass fabric had a flexural strength of 21,800 psi. and a polypropylene-glass laminate prepared from gamma-methacryloxypropyltrimethoxysilane finished glass fabric had a flexural strength of 17,900 psi.

EXAMMPLE 18

A clear, stable 2 wt.% aqueous azido-silane product solution was formed by dissolving 2.8 grams of $H_2NCH_2CH_2NHCH_2CH_2NHCH_2CH_2CH_2Si(OCH_3)_3$ in 490 grams of water at room temperature and then adding 7.2 grams of 3-(azidosulfonyl) benzoic acid with vigorous stirring.

EXAMPLE 19

The azido-silane product solution of Example 18 was used to prepare a glass-polypropylene laminate by following the procedure of Example 11.

The test specimens showed an initial flexural strength of 23,000 psi. and a flexural stength of 18,700 psi. after 16 hours in 122° F. water. By comparison a polypropylene-glass laminate prepared from unfinished heat-cleaned fabric had an initial flexural strength of 12,700 psi. and a flexural stength of 9,600 psi. after 16 hours in 122° F. water; a polypropyleneglass laminate prepared from $H_2NCH_2CH_2NHCH_2CH_2NHCH_2CH_2CH_2Si(OCH_3)_3$ finished glass fabric had an initial flexural strength of 19,700 psi. and a flexural strength of 14,500 psi. after 16 hours in 122° F. water; and a polypropylene-glass laminate prepared from 3-(azidosulfonyl)benzoic acid finished glass fabric had an initial flexural strength of 23,700 psi. and a flexural strength of 11,000 psi. after 16 hours in 122° F. water.

EXAMPLE 20

A 2 wt.% aqueous azido-silane product solution of gamma-glycidoxypropyltrimethoxysilane modified polyamide polymer and 3-(azidosulfonyl) benzoic acid prepared as in Example 6 was used to prepare a glass-polypropylene laminate by following the procedure of Example 11.

The test specimens showed an initial flexural strength of 24,500 psi. and a flexural strength of 19,600 psi. after 16 hours in 122° F. water. By comparison a polypropylene-glass laminate prepared from unfinished heat-cleaned glass fabric had an initial flexural strength of 12,700 psi. and a flexural strength of 9,600 psi. after 16 hours in 122° F. water; a polypropylene-glass laminate prepared from azido-free gammaglycidoxypropyltrimethoxysilane modified polyazamide polymer finished glass fabric had an initial flexural strength of 18,900 psi. and a flexural strength of 16,800 psi. after 16 hours in 122° F. water; and a polypropylene-glass laminate prepared from 3-(azidosulfonyl)benzoic acid finished glass fabric had an initial flexural strength of 23,700 psi. and a flexural strength of 11,000 psi. after 16 hours in 122° F. water.

EXAMPLE 21

A 5 wt.% aqueous azido-silane product solution prepared according to Example 1 using 66 grams of gammaaminopropyltriethoxysilane and 67 grams of 3-(azidosulfonyl)benzoic acid was used to coat water-sized fiber glass virgin roving. The treated fiber glass strand was then dried and chopped into one-fourth inch long strands. The coated fiber glass showed a loss-on-ignition of 0.45 wt.%

EXAMPLE 22

Azido-silane coated chopped fiber glass strand prepared by repeating Example 21 was mixed with high density polyethylene resin and the mixture (30 wt.% glass and 70 wt.% polyethylene) was injection molded at 450° F. (mold temperature 120° F., injection pressure 13,000 psi.) using a three ounce Van Dorn injection molder of 75 ton clamp pressure to yield test specimens of glass-reinforced polyethylene.

The test specimens showed a flexural strength of 14,300 psi., a tensile strength of 9,500 psi., a heat-distortion temperature of 252° F. and a falling dart impact of 20 inch pounds. By comparison glass reinforced polyethylene specimens prepared from untreated water-sized fiber glass chopped virgin roving and high density polyethylene showed a flexural strength of 7,700 psi., a tensile strength of 4,700 psi, and a falling dart impact of 8 inch pounds, while test specimens prepared from a commercial chopped fiber glass roving (specified for use in high density polyethylene) and high density polyethylene showed a flexural strength of 13,800 psi., a tensile strength of 9,900 psi., a heat-distortion temperature of 253° F. and a falling dart impact of 10 inch pounds.

EXAMPLE 23

Azido-silane coated chopped fiber glass strand prepared by repeating Example 21 was mixed with polypropylene resin and the mixture (30 wt.% glass and 70 wt.% polypropylene) was injection molded at 480° F. (mold temperature 120° F., injection pressure 12,000 psi.) using a three ounce Van Dorn injection molder of 75 ton clamp pressure to yield test specimens of glass-reinforced polypropylene.

The test specimens showed a flexural strength of 11,300 psi., a tensile strength of 7,400 psi. and a heat-distortion temperature of 297° F. By comparison glass reinforced polypropylene specimens prepared from untreated water-sized fiber glass chopped virgin roving and polypropylene showed a flexural strength of 8,900 psi., a tensile strength of 5,300 psi. and a heat-distortion temperature of 197° F; while test specimens prepared from a commercial chopped fiber glass roving (specified for use in polypropylene) and polypropylene showed a flexural strength of 10,400 psi, a tensile strength of 6,300 psi. and a heat-distortion temperature of 216° F.

EXAMPLE 24

Azido-silane coated chopped fiber glass strand prepared by repeating Example 21 was mixed with nylon 6 resin and the mixture (30 wt.% glass and 70 wt.% nylon) was injection molded at 550° F. (mold temperature 150° F., injection pressure 14,000 psi.) using a three ounce Van Dorn injection molder of 75 ton clamp pressure to yield test specimens of glass-reinforced nylon.

The test specimens showed a flexural strength of 34,500 psi., a tensile strength of 21,900 psi. and a heat-distortion temperature of 397° F. By comparison test specimens prepared from a commercial chopped fiber glass roving, (specified for use in nylon) and nylon showed a flexural strength of 33,100 psi., a tensile strength of 22,800 psi. and a heat-distortion temperature of 410° F.

EXAMPLE 25

Azido-silane coated chopped fiber glass strand prepared by repeating Example 21, but using a 5 wt.% aqueous-silane product solution of the gamma-glycidoxypropyltrimethoxysilane modified polyazamide polymer and 3-(azidosulfonyl)benzoic acid prepared as in Example 6, was used, mixed with polypropylene resin and the mixture (30 wt.% glass and 70 wt.% polypropylene was injection molded at 480° F. (mold temperature 120° F., injection pressure 12,000 psi.) using a three ounce Van Dorn injection molder of 75 ton clamp pressure to yield test specimens of glass-reinforced polypropylene.

The test specimens showed a flexural strength of 8,800 psi., a tensile strength of 6,200 psi. and a heat-distortion temperature of 307° F. By comparison glass reinforced polypropylene prepared from untreated water-sized fiber glass chopped virgin roving and polypropylene had a flexural strength of 8,900 psi., a tensile strength of 5,300 psi. and a heat-distortion temperature of 197° F.; further test specimens prepared from azido-free gamma-glycidoxypropyltrimethoxysilane modified polyazamide polymer coated water-sized fiber glass chopped virgin roving and polypropylene showed a flexural strength of 8,400 psi, a tensile strength of 4,600 psi. and a heat-distortion temperature of 267° F.; while test specimens prepared from a commercial chopped fiber glass roving (specified for use in polypropylene) and polypropylene showed a flexural strength of 10,400 psi., a tensile strength of 6,300 psi. and a heatdistortion temperature of 216° F.

EXAMPLE 26

An ethanolic azido-silane product solution was prepared according to Example 1 using 9.0 grams of gamma-aminopropyltriethoxysilane, 9.2 grams of 3-(azidosulfonyl) benzoic acid and 150 ml. of 190 proof ethanol. The clear stable product solution was used to coat talc, Wollastonite, feldspar and silica fillers in a twin-shell blender equipped with an intensifier bar. The treated fillers were then dried for two hours at 100° C. and used as detailed in Examples 27 to 31.

EXAMPLE 27

Four pounds of talc treated as described in Example 26 were mixed with polypropylene resin and the mixture (50 wt.% talc and 50 wt.% polypropylene) was injection molded at 480° F. (mold temperature 120° F, injection pressure 12,000 psi.) using a three ounce Van Dorn injection molder of 75 ton clamp pressure to yield test specimens of talc-filled polypropylene.

The test specimens showed a flexural strength of 8,400 psi. and a tensile strength of 4,500 psi. By comparison test specimens prepared from untreated talc and polypropylene showed a flexural strength of 7,200 psi. and a tensile strength of 3,700 psi; test specimens prepared from gamma-aminopropyltriethoxysilane treated talc and polypropylene showed a flexural strength of 6,900 psi. and a tensile strength of 3,500 psi; while test specimens prepared from 3-(azidosulfonyl) benzoic acid treated talc and polypropylene showed a flexural strength of 4,200 psi.

EXAMPLE 28

Four pounds of talc tested as described in Example 26 were mixed with nylon 6 resin and the mixture (50 wt.% talc and 50 wt.% nylon) was injection molded at 500° F. (mold temperature 150° F., injection pressure 1300 psi.) using a three ounce Van Dorn injection molder of 75 ton clamp pressure to yield test specimens of talc-filled nylon.

The test specimens showed a flexural strength of 15,500 psi. and a tensile strength of 9,900 psi. By comparison test specimens prepared from untreated talc and nylon showed a flexural strength of 15,000 psi. and a tensile strength of 9,300 psi; and test specimens prepared from gamma-aminopropyltriethoxysilane treated talc and nylon showed a flexural strength of 16,100 psi. and a tensile strength of 9,800 psi.

EXAMPLE 29

Four pounds of Wollastonite treated as described in Example 26 were mixed with polypropylene resin and the mixture (50 wt.% Wollastonite and 50 wt.% polypropylene) was injection molded at 480° F. (mold temperature 120° F., injection pressure 12,000 psi.) using a three ounce Van Dorn injection molder of 75 ton clamp presser to yield test specimens of Wollastonite-filled polypropylene.

The test specimens showed a flexural strength of 8,800 psi. and a tensile strength of 4,500 psi. By comparison test specimens prepared from untreated Wollastonite and polypropylene showed a flexural strength of 6,500 psi. and a tensile strength of 3,200 psi.; test specimens prepared from gamma-aminopropyltriethoxysilane treated Wollastonite and polypropylene showed a flexural strength of 6,900 psi. and a tensile strength of 3,500 psi; while test specimens prepared from 3-(azidosulfonyl) benzoic acid treated Wollastonite and polypropylene showed a flexural strength of 7,900 psi. and a tensile strength of 4,200 psi.

EXAMPLE 30

Four pounds of feldspar treated as described in Example 26 were mixed with polypropylene resin and the mixture (50 wt.% feldspar and 50 wt.% polypropylene) was injection molded at 480° F. (mold temperature 120° F. injection pressure 12,000 psi.) using a three ounce Van Dorn injection molder of 75 ton clamp pressure to yield test specimens of feldspar-filled polypropylene.

The test specimens showed a flexural strength of 7,700 psi. and a tensile strength of 4,100 psi. By comparison test specimens prepared from untreated feldspar and polypropylene showed a flexural strength of 5,200 psi. and a tensile strength of 2,400 psi. and test specimens prepared from gamma-aminopropyltriethoxysilane treated feldspar and polypropylene showed a flexural strength of 5,900 psi. and a tensile strength of 2,900 psi.

EXAMPLE 31

Four pounds of silica treated as described in Example 26 were mixed with polypropylene resin and the mixture (50 wt.% silica and 50 wt.% of polypropylene) was injection molded at 480° F. (mold temperature 120° F., injection pressure 12,000 psi.) using a three ounce Van Dorn injection molder of 75 ton clamp pressure to yield specimens of silica-filled polypropylene.

The test specimens showed a flexural strength of 8,400 psi. and a tensile strength of 4,300 psi. By comparison test specimens prepared from untreated silica and polypropylene showed a flexural strength of 5,900 psi. and a tensile strength of 2,800 psi. and test specimens prepared from gamma-aminopropyltriethoxysilane treated silica and polypropylene showed a flexural strength of 6,200 psi. and a tensile strength of 3,000 psi.

EXAMPLE 32

An ethanolic azido-silane product solution was prepared according to Example 1 using 4 grams of gammaaminopropyltriethoxysilane, 6 grams of 3,5-di(azidosulfonyl)benzoic acid and 150 ml. of 190 proof ethanol.

The clear stable product solution was used to coat Wollastonite filler in a twin-shell blender equipped with an intensifier. The treated filler was then dried for 2 hours at 100° C. 2.2 pounds of the treated Wollastonite were mixed with polypropylene resin and the mixture (50 wt.% Wollastonite and 50 wt.% polypropylene was injection molded at 480° F. (mold temperature 120° F., injection pressure 15,000 psi) using a three ounce Van Dorn injection molder to yield test specimens of Wollastonite-filled polypropylene.

The test specimens showed a flexural strength of 9,900 psi. and a tensile strength of 5,200 psi. By comparison test specimens prepared from untreated Wollastonite and polypropylene showed a flexural strength of 6,500 psi and a tensile strength of 3,200 psi. and test specimens prepared from gamma-aminopropyltriethoxysilane treated Wollastonite and polypropylene showed a flexural strength of 3,500 psi.

Various modifications and variations of this invention will be obvious to a worker skilled in the art and it is to be understood that such modifications and variations are to be included within the purview of this application and the spirit and scope of the appended claims.

What is claimed is:

1. A solubilized azido-containing silane composition of matter produced by a process which comprises reacting in the presence of a solvent (a) an azido-containing compound selected from the group consisting of carboxylic acids of the formula

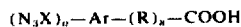

and the ammonium salts of said acids, wherein X is a radical selected from the group consisting of sulfonyl and formyl radicals, $a$ is an integer of from 1 to 2, Ar is an aryl or hydroxy-substituted aryl radical, R is an alkylene radical and $n$ has a value of 0 or 1; and (b) an amino-containing silane having the formula

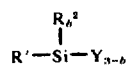

wherein $R^2$ is a monovalent hydrocarbon radical, $b$ has a value of from 0 to 2, Y is a hydrolyzable group selected from the class consisting of alkoxy and aryloxy radicals, and R' is an organic radical directly bonded to the silicon atom of said silane through a carbon to silicon bond, said organic radical further containing at least one nitrogen atom, said solvent being present in an amount sufficient to solubilize the azido-containing silane product of (a) and (b).

2. A solubilized azido-containing silane composition of matter as defined in claim 1, wherein the solvent is selected from the group consisting of water, alcohols, ethers and ketones.

3. A solubilized azido-containing silane composition of matter as defined in claim 2, wherein the solvent is water.

4. A solubilized azido-containing silane composition of matter as defined in claim 2, wherein X is a sulfonyl radical, $a$ is 1; Ar is phenylene or hydroxyphenylene; $n$ is 0; $b$ is 0; Y is an alkoxy radical having from 1 to 12 carbon atoms and R' is an organic radical selected from the group consisting of aminoalkylene, aminoaryl, alkylene polyamine and polyazamide radicals.

5. A solubilized azido-containing silane composition of matter as defined in claim 4, wherein the solvent is water.

6. A solubilized azido-containing silane composition of matter as defined in claim 4, wherein Y is a lower alkoxy radical having from 1 to 4 carbon atoms and R' is an amino radical of the formula

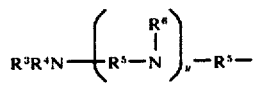

wherein $R^3$, $R^4$ and $R^6$ individually represent a radical selected from the group consisting of hydrogen and a monovalent hydrocarbon radical having from 1 to 12 carbon atoms, at least one $R^3$, $R^4$ and $R^6$ group being hydrogen; each $R^5$ group individually represents a divalent alkylene radical having from 1 to 10 carbon atoms; and $y$ is 0 or a positive integer.

7. A solubilized azido-containing silane composition of matter as defined in claim 6, wherein the azido-containing compound is a carboxylic acid; Ar is a phenylene radical; $R^3$, $R^4$ and $R^6$ individually represent a radical selected from the group consisting of hydrogen and a methyl radical; $y$ has a value of 0 to 4; and each $R^5$ group individually represents a divalent alkylene radical having from 2 to 6 carbon atoms.

8. A solubilized azido-silane compositon of matter as defined in claim 7 wherein the solvent is water.

9. A solubilized azido-silane composition of matter as defined in claim 8 wherein the azido-containing compound is 3-(azidosulfonyl) benzoic acid and the amino-containing silane is selected from the group consisting of gamma-aminopropyltriethoxysilane and N-beta-(aminoethyl)-gamma-aminopropyltrimethoxysilane.

10. An azido-containing silane composition of matter as defined in claim 1, obtained upon removal of the solvent.

11. An azido-containing silane composition of matter as defined in claim 3 obtained upon removal of the water.

* * * * *